United States Patent [19]

Iba et al.

[11] 4,439,023
[45] Mar. 27, 1984

[54] OPTICAL SYSTEM FOR OPHTHALMOLOGICAL INSTRUMENTS

[75] Inventors: Youich Iba; Ken-ichi Nakahashi; Masaki Matsubara, all of Hachiouji, Japan

[73] Assignee: Olympus Optical Co., Ltd., Tokyo, Japan

[21] Appl. No.: 260,395

[22] Filed: May 4, 1981

[30] Foreign Application Priority Data

May 8, 1980 [JP] Japan ................................. 55-59994

[51] Int. Cl.³ .......................... A61B 3/14; G03B 29/00
[52] U.S. Cl. ..................................... 351/206; 354/62; 351/214
[58] Field of Search ............... 351/214, 206, 207, 208; 354/62

[56] References Cited

U.S. PATENT DOCUMENTS 4,149,787  4/1979  Kobayashi et al. ................. 351/206

*Primary Examiner*—John K. Corbin
*Assistant Examiner*—Rodney B. Bovernick
*Attorney, Agent, or Firm*—Cushman, Darby & Cushman

[57] ABSTRACT

A compactly designable optical system for ophthalmological instruments comprising an illumination system so adapted as to illuminate a fundus with rays having passed through a ring slit and been focused on the cornea of an eyeball to be examined, and an observation/-photographing system so adapted as to permit observing and photographing an image of said eyeball with a small reflector mirror arranged in said illumination system so as to be inclined with regard to the optical axis thereof and a relay lens for focusing the rays which are reflected by the fundus, passing through said objective lens and reflected by said small reflector mirror.

4 Claims, 3 Drawing Figures

U.S. Patent  Mar. 27, 1984  4,439,023
PRIOR ART FIG. 1
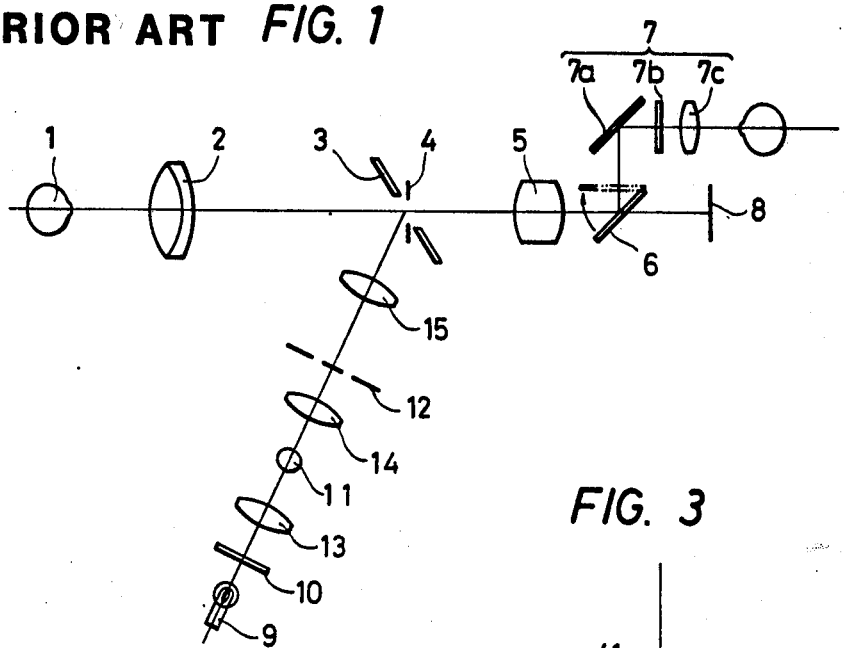
FIG. 3
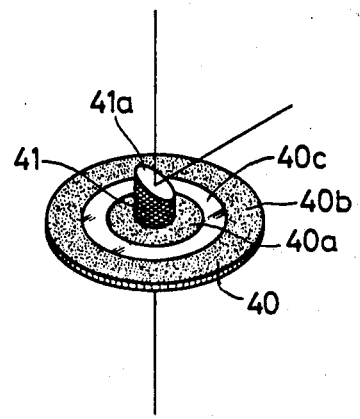
FIG. 2
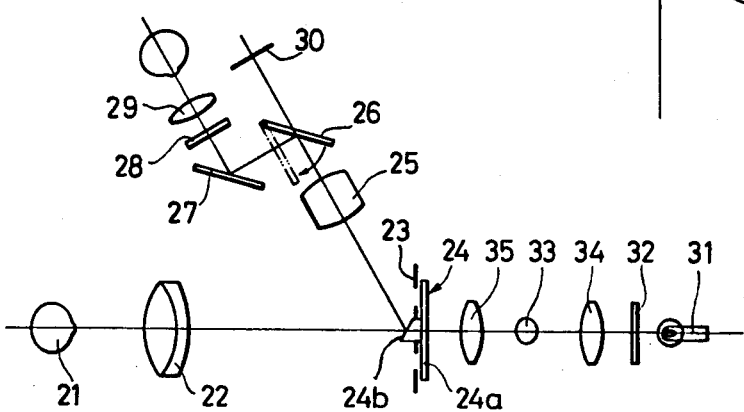

OPTICAL SYSTEM FOR OPHTHALMOLOGICAL INSTRUMENTS

BACKGROUND OF THE INVENTION (a) Field of the Invention

The present invention relates to an improvement of an optical system for ophthalmological instruments such as fundus cameras.

(b) Field of the Invention

The conventional fundus camera has such a composition as shown in FIG. 1 wherein the reference numeral 1 represents an eyeball to be examined, the reference numeral 2 designates an objective lens, the reference numeral 3 denotes a mirror having an aperture, the reference numeral 4 represents a stop, the reference numeral 5 designates a relay lens, the reference numeral 6 denotes a switching mirror, the reference numeral 7 represents an eyepiece, the reference numeral 8 designates a film surface, the reference numeral 9 denotes a light source for observation, the reference numeral 10 represents a heat-preventive filter, the reference numeral 11 designates a photographing light source such as strobo tube, the reference numeral 12 denotes a ring slit, reference numerals 13 and 14 represent collector lenses, and the reference numeral 15 designates a lens for projecting an image of the ring slit. In this optical system, the light source 9 is always lit and emits rays which are focused by the collector lens 13 so as to form an image of the light source 9 at a position substantially the same as that of the photographing light source 11. This image of the light source is focused again by the collector lens 14 at a position in the vicinity of the ring slit 12. Therefore, the ring slit functions as a secondary light source in the optical system arranged at the subsequent stage. The rays having passed through this ring slit are projected by the projector lens 15 to a position in the vicinity of the mirror 3 having an aperture. This image of the ring slit is further projected by the objective lens 2 to the cornea surface of the eyeball to be examined to achieve ring-shaped illumination already known to those skilled in the art. The illuminating rays scattered by the fundus illuminated in this way are projected through the cornea and focused by the objective lens 2 so as to form an image of the fundus at a position between the objective lens 2 and mirror 3 having an aperture. This image of the fundus is passed through the stop 4, focused by the relay lens 5 and reflected by the switching reflector mirror 7 and reflector mirror 7a, and formed again on a focusing plate 7b for observation through the eyepiece 7c. When the switching mirror 6 is turned to the position indicated by the chain line, the image of the fundus is formed on the film surface 8 for photographing.

In order to design a fundus camera comprising such an optical system more compact, there can be considered a method to design the lenses more compact, another method to shorten the total length of the lens system as a whole, a third method to shorten focal length of the lens system as a whole and so on. However, all of these methods offers possibility to design the optical system compactly only within a certain limited range.

SUMMARY OF THE INVENTION

An object of the present invention is to provide an optical system for ophthalmological instruments which comprises a small reflector mirror and can be designed compact.

A further object of the present invention is to provide an optical system for ophthalmological instruments comprising an illumination system so adapted as to illuminate fundus of an eyeball to be examined with illumination rays having passed through a ring slit and an objective lens, and an observation/photographing system so adapted as to permit observing and photographing an image of the fundus of said eyeball to be examined with a small reflector mirror arranged in said illumination system so as to be inclined with regard to the optical axis thereof and a relay lens for focusing the rays reflected by the fundus, passing through said objective lens and reflected by said small reflector mirror.

BRIEF DESCRIPTION OF THE DRAWINGS

FIG. 1 shows a sectional view illustrating the composition of the optical system for the conventional fundus camera;

FIG. 2 shows a sectional view illustrating composition of the optical system for fundus camera according to the present invention; and FIG. 3 shows a perspective view of an optical element which serves both as a small reflector mirror and a ring slit to be used in the optical system according to the present invention.

DETAILED DESCRIPTION OF THE PREFERRED EMBODIMENT

Now, the optical system for ophthalmological instruments according to the present invention will be described more detailedly with reference to a preferred embodiment shown in the accompanying drawings.

In FIG. 2, the reference numeral 21 represents an eyeball to be examined, the reference numeral 22 designates an objective lens, the reference numeral 23 denotes a ring slit, the reference numeral 24 represents an optical element having a small reflecting surface so constructed as to be described later, the reference numeral 25 designates a relay lens, the reference numeral 26 denotes a switching mirror, the reference numeral 27 represents a reflector mirror, the reference numeral 28 designates a focusing plate, the reference numeral 29 denotes an eyepiece and the reference numeral 30 represents a film surface. In addition, the reference numeral 31 designates a light source for observation, the reference numeral 32 denotes a heat-preventive filter, the reference numeral 33 represents a light source for photographing such as a strobo tube, and the reference numerals 34 and 35 designate collector lenses respectively.

The optical element 24 used in the optical system shown in FIG. 2 is made of a transparent disc 24a at the center of which is formed a protrusion 24b having a reflecting surface slanted toward the objective lens.

In the optical system comprising such an optical element 24 shown in FIG. 2, the rays emitted from the light source 31 pass through the transparent disc 24a and are focused to form an image of the light source in the vicinity of the ring slit 23 in the same manner as that in the conventional optical system shown in FIG. 1. The rays having passed through the ring slit 23 are focused by the objective lens 22 so as to form an image in the vicinity of the cornea for illuminating the fundus of the eyeball to be examined.

A ring-shaped illumination is achieved in this way. Subsequently, the rays scattered by the fundus pass through the objective lens 22 and are reflected on the small reflecting surface of the protrusion 24b, thereafter passing through the relay lens 25 and being used for observation or photographing in the same manner as that in the conventional optical system shown in FIG. 1.

Since the ring slit 23 and the cornea of the eyeball to be examined are kept in a conjugate relationship with regard to the objective lens 22 in the optical system based on the ring illumination method according to the present invention described above, the rays reflected by the cornea return to the circular aperture of the ring slit. Therefore, the rays reflected by the cornea surface are not reflected by the small reflecting surface of the optical element 24 and do not enter the photographing/observation system. Since the small reflecting surface functions to separate and select the image of the fundus from the rays reflected by the cornea surface so as to make the former to follow a different optical path, the image of the fundus formed on the film surface or the focusing plate is free from flare.

Since the optical system according to the present invention adopts a small reflector mirror instead of the mirror having an aperture to separate the illumination system from the photographing/observation system as described above, the illumination system is laid out linearly.

Though it may seem that a simple small reflector mirror inclined with regard to the optical axis of the objective lens 22 can be used in place of the optical element having the above-described construction, the latter is more convenient when a fixing mean for it is taken into consideration.

FIG. 3 shows a different example of the optical element 24 having a small reflecting surface which is made of a transparent disc 40 such as a glass disc having a central portion 40a, a circumferential portion 40b which are painted black or bonded to light-shielding plates so as to form light-shielding portions, and a ring-like transparent portion 40c reserved therebetween so as to serve as a ring slit. Arranged on the central light-shielding portion 40a is a protrusion 41 having a top reflecting surface so slanted with regard to the optical axis as to form a reflecting surface 41a.

The optical system according to the present invention permits ring-shaped illumination and observation of fundus without using the conventional reflector mirror having an aperture. As a result, said optical system is so adapted so as to allow the objective lens to form an image of the ring slit on the cornea surface of the eyeball to be examined without forming it in the vicinity of the reflector mirror having an aperture. Said optical system therefore requires no lens which functions to project an image of the ring slit to the vicinity of the reflector mirror having an aperture. Further, the optical element 24 can have the function described below when it has the central light-shielding portion larger than the reflecting surface. When an image of the ring slit is formed on the cornea surface with the objective lens, the image quality is apt to be degraded due to aberrations produced by the objective lens. Further, position of the eyeball to be examined may deviate from the position perfectly conjugate with the ring slit. Moreover, the rays reflected by the cornea surface are subjected to influence due to aberrations produced by the objective lens. Due to these influences, the image of fundus cannot be separated and selected completely from detrimental rays by the small reflecting surface only. When the central light-shielding portion is larger than the reflecting surface and forms a dead zone which does not transmit neither the rays reflected by the fundus or the illumination rays between the sections forming the paths for both the kinds of rays, the optical element can completely separate both the types of rays to make the image of fundus free from flare, etc. even when its quality is degraded a little. The optical element 24 can therefore eliminate the necessity of the stop 4 used in the optical system shown in FIG. 1.

As is understood from the foregoing descriptions, the optical system according to the present invention makes it possible to arrange a small reflecting surface in place of the mirror having an aperture used in the conventional fundus camera and place a ring slit directly in the vicinity of said reflecting surface. Said optical system therefore eliminates the necessity of the space which was conventionally required to project an image of the ring slit to the vicinity of the mirror having an aperture by using a projector lens, thereby making it possible to design the optical system more compact or simplify the composition thereof. In addition, the optical system uses no projector lens and eliminates the problem of deformation of image due to aberrations produced by a projector lens, thereby assuring optical characteristic more excellent than that of the conventional optical system.

What is claimed is:

1. An optical system for ophthalmological instruments comprising an illumination system comprising a light source, collector lenses, a ring slit having a central light shielding portion arranged in close proximity an image of said light source formed with said collector lenses and an objective lens so arranged as to form an image of said ring slit in close proximity to the cornea of an eyeball to be examined, and a photographing/observation system comprising said objective lens, a small reflector mirror arranged in close proximity to said ring slit and positioned on and inclined with regard to the optical axis of said objective lens and a relay lens for focusing the rays reflected from the fundus of the eyeball to the examined after said rays have passed through said objective lens and been reflected by said small reflecting mirror.

2. An optical system for ophthalmological instruments according to claim 1 wherein said small reflector mirror has a diameter smaller than that of the central light-shielding portion of said ring slit.

3. An optical system for ophthalmological instruments according to claim 1 wherein said small reflector mirror consists of a transparent plate and a protrusion protruding from said transparent plate and having a reflecting surface.

4. An optical system for ophthalmological instruments according to claim 1 wherein said ring slit and said small reflector mirror are composed as a member consisting of a transparent plate forming light-shielding portions while leaving a ring-like transparent portion and a protrusion protruding from said transparent plate and having a reflecting surface.

* * * * *